(12) United States Patent
Inoue

(10) Patent No.: US 6,986,991 B1
(45) Date of Patent: Jan. 17, 2006

(54) METHOD OF ANALYZING INTESTINAL FLORA AND ANALYTICAL APPARATUS

(75) Inventor: Takakazu Inoue, Ushiku (JP)

(73) Assignee: Sanyo Electric Co., Ltd., Moriguchi (JP)

( * ) Notice: Subject to any disclaimer, the term of this patent is extended or adjusted under 35 U.S.C. 154(b) by 310 days.

(21) Appl. No.: 10/069,977

(22) PCT Filed: Aug. 31, 2000

(86) PCT No.: PCT/JP00/05943
§ 371 (c)(1),
(2), (4) Date: Mar. 13, 2002

(87) PCT Pub. No.: WO01/20032
PCT Pub. Date: Mar. 22, 2001

(30) Foreign Application Priority Data

Sep. 16, 1999 (JP) .......................................... 11-262590
Nov. 22, 1999 (JP) .......................................... 11-330924

(51) Int. Cl.
*C12Q 1/68* (2006.01)
*C12P 19/34* (2006.01)

(52) U.S. Cl. ........................ 435/6; 435/91.2; 435/91.52
(58) Field of Classification Search ..................... 435/6, 435/91.2, 91.52, 5; 335/77, 78, 76; 536/23.1, 536/24.3
See application file for complete search history.

(56) References Cited

U.S. PATENT DOCUMENTS

| | | | | | |
|---|---|---|---|---|---|
| 4,800,159 | A | * | 1/1989 | Mullis et al. | 435/172.3 |
| 5,498,392 | A | * | 3/1996 | Wilding et al. | 422/68.1 |
| 5,753,467 | A | | 5/1998 | Jensen et al. | 435/91.2 |
| 5,846,783 | A | | 12/1998 | Wu et al. | 425/91.2 |
| 6,274,306 | B1 | * | 8/2001 | Inoue | 435/4 |
| 6,287,769 | B1 | * | 9/2001 | Inoue | 435/6 |

FOREIGN PATENT DOCUMENTS

| | | |
|---|---|---|
| DE | 199 14 461 A1 | 10/1999 |
| JP | 11-123093 A | 5/1999 |
| JP | 11-127898 A | 5/1999 |
| JP | 11-127899 A | 5/1999 |
| JP | 11-151097 A | 6/1999 |
| WO | WO 97/31256 | 8/1997 |

OTHER PUBLICATIONS

Hamad et al. Journal of Applied Microbiology, 1997, vol. p. 746-770.*

W. Day et al.; "Use of an Arbitrarily Primed PCR Product in the Development of a Campylobacter Jejuni–Specific PCR," Applied and Environmental Microbiology; Mar. 1997; pp. 1019–1023.

C. Eichner et al.; "Thermal Gradient Gel Electorphoresis Analysis of Bioprotection From Pollutant Shocks in the Activated Sludge Microbial Community", Applied and Environmental Microbiology; Jan. 1999; vol. 65, No. 1, pp. 102–109.

F. Schwieger et al.; "A New Approach to Utilize PCR–Single–Stranded–Conformation Polymorphism for 16S rRNA Gene–Based Microbial Community Analysis" Applied and Environmental Microbiology; Dec. 1998, vol. 64, No. 12, pp. 4870–4876.

M. Islam et al.; "Detection of *Shigellae* From Stools of Dysentery Patients by Culture and Polymerase Chain Reaction Techniques"; J. Diarrhoel Dis. Res.; Dec. 1998, vol. 16, No. 4, pp. 248–251.

F. Ausubel et al.; "Current Protocols in Molecular Biology"; Supplement 9; 1990; pp. 2.4.1 to 2.4.2.

A. Hiraishi et al.; "Restriction Pattern Analysis by High–Performance Liquid Chromatography of PCR–Amplified 16S rDNA Fragments From Scum–Forming Bacteria in Activated Sludge"; Microbes and Environments; vol. 12; No. 3, 1997, pp. 57–68.

B. Alberts et al.; "Molecurlar Biology of the Cell", Third Edition; p. 340.

"Lectures of Second Symposium of Japan Society of Water Environment" Sep. 13, 1999, pp. 54–55, and partial translation.

"Information Processing"; IPSJ Magazine; vol. 40, No. 3; Mar. 1999; pp. 320–325, and partial translation.

\* cited by examiner

*Primary Examiner*—Kenneth R. Horlick
*Assistant Examiner*—Joyce Tung
(74) *Attorney, Agent, or Firm*—Armstrong, Kratz, Quintos, Hanson & Brooks, LLP

(57) ABSTRACT

A method of analyzing intestinal bacteria flora which comprises: extracting a sample from a subject; extracting bacteria to prepare a bacteria suspension; extracting DNAs of bacteria from the bacteria suspension to prepare a DNA extract liquid; amplifying a specific region such as 16S rDNA using the DNA extract liquid; fractionating the amplified fragments by electrophoresis to obtain a fractional pattern; and comparing the fractional pattern with preliminarily obtained electrophoretic patterns of amplified fragments of intestinal bacteria flora, thereby analyzing the intestinal bacteria flora of the subject.

6 Claims, 8 Drawing Sheets

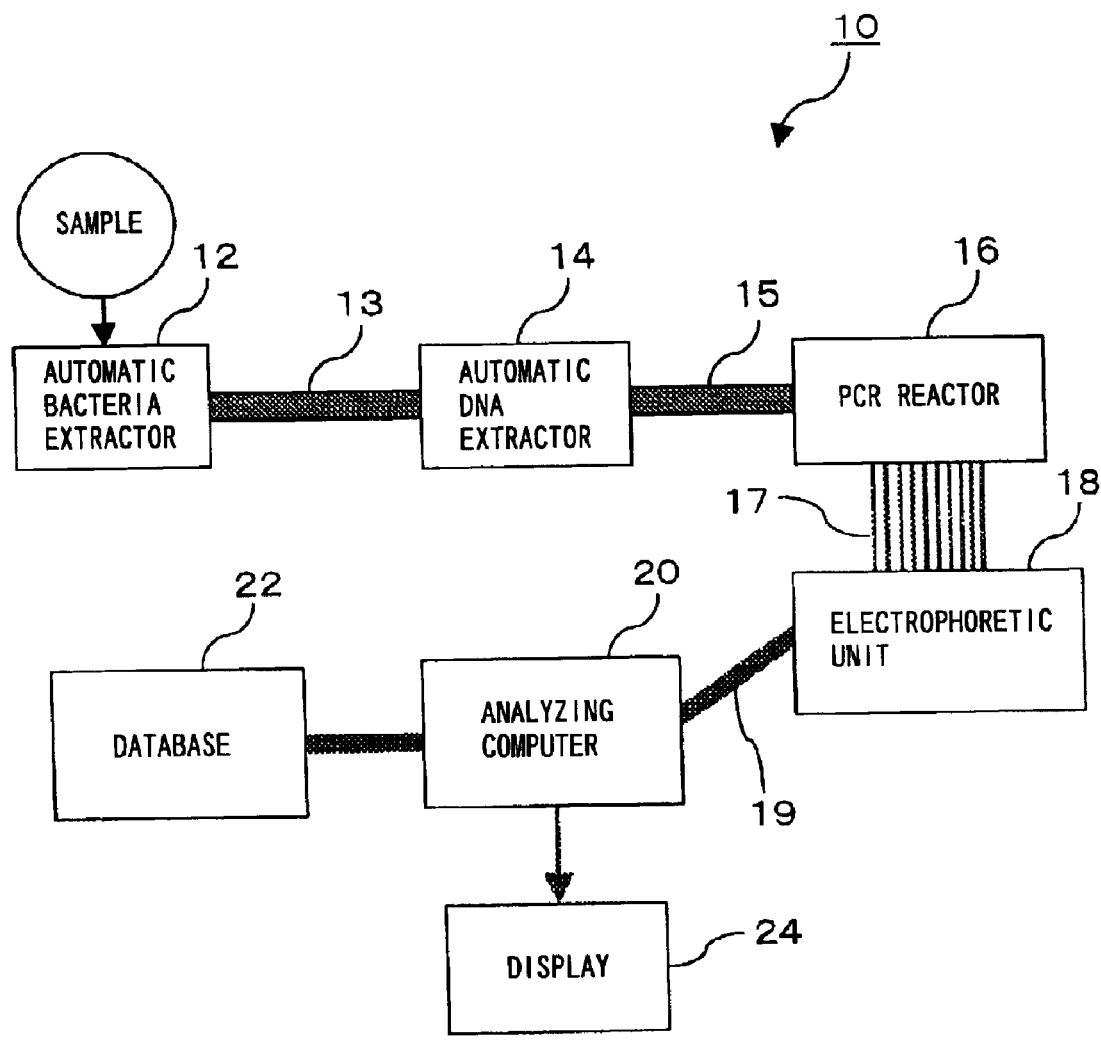
F I G. 4

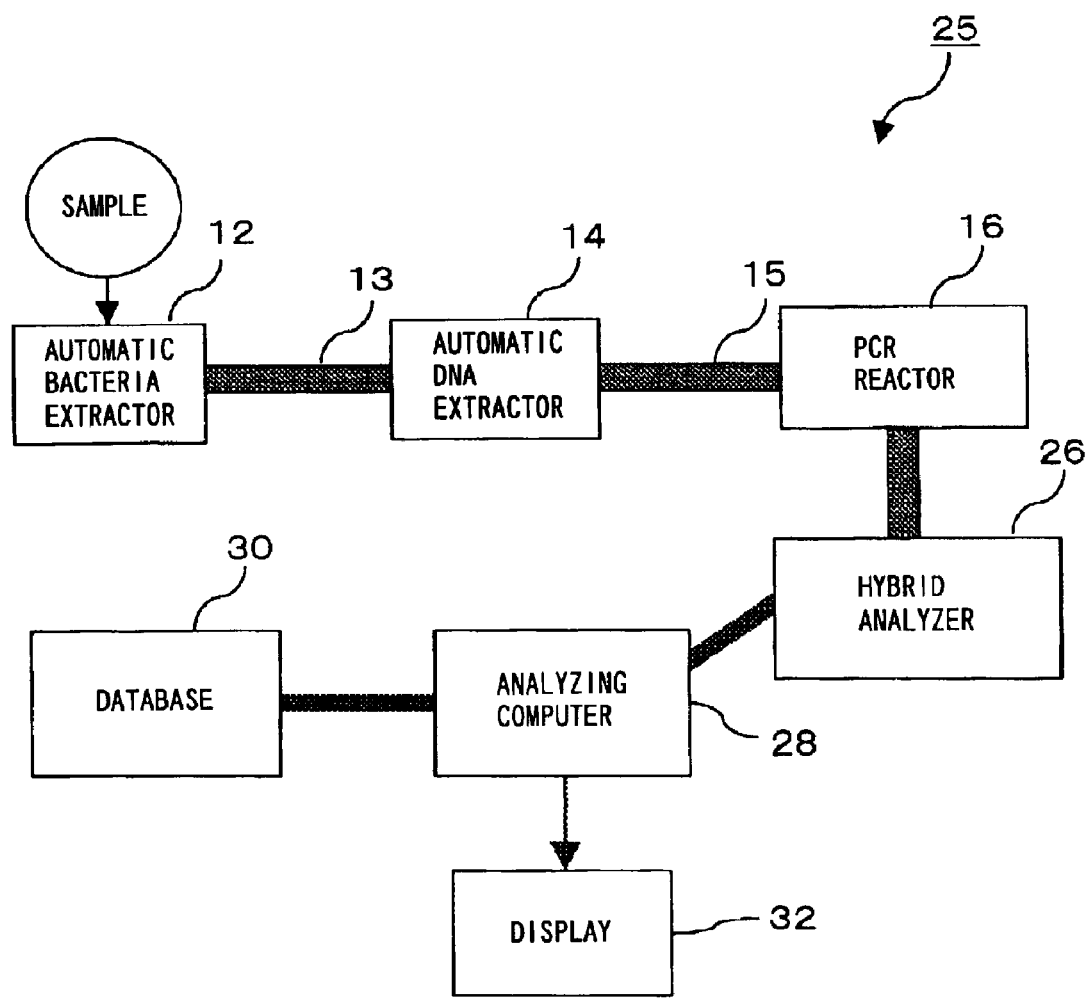
F I G. 5

US 6,986,991 B1

METHOD OF ANALYZING INTESTINAL FLORA AND ANALYTICAL APPARATUS

TECHNICAL FIELD

The present invention relates to a method and an apparatus for analyzing an intestinal bacterial flora (intestinal flora) of a subject.

BACKGROUND ART

Normal bacteria called intestinal bacteria are present in the intestine, and a distributed state of these bacteria is referred to as an intestinal bacterial flora. A *Salmonella* relative to *colibacillus* belonging to *Enterobacteriaceae* etc., a *Bacteroides*, a *Eubacterium*, a *Bifidobacterium*, a *Peptostreptococcus*, a *Clostridium*, a *Lactobacillus* and the like are included in the intestinal bacteria.

While these intestinal bacteria perform ancillary parts for digestion of food and contribute to maintenance of physical condition by suppressing growth of alien pathogenic fungi etc., such an intestinal bacterial flora is not constant in each individual but varies with the age, food habituation etc. of the host. It is known that the intestinal bacteria flora varies with a disease, mental stress or the like in the same individual.

When analyzing such an intestinal bacterial flora, cultivation has been utilized in general. That is, each intestinal bacterium has been identified on the basis of the characters of the bacterium by planting a sample such as dejection of the subject in a selective medium or a non-selective medium or the like, cultivating each medium in accordance with growth conditions for each bacterium and dyeing the growing bacterium or the like.

However, it is said that intestinal bacterial groups amount to 100 types ("Intestinal Flora and Probiotics" (INTESTINAL FLORA AND PROBIOTICS)", Proceedings of V. Symposium of Intestinal Flora, Tokyo, 1996, Japan Scientific Societies Press), it is extremely difficult to analyze these numerous intestinal bacterial groups by cultivation, and it follows that the range of analyzable bacteria is also limited. Even if analysis is possible as to a constant range of bacterial groups, it has been work requiring time and labor for cultivating and identifying a large number of bacteria.

Also in the bacterium, on the other hand, genetic information where the qualities of the respective bacteria are recorded is coded in chromosomes as DNA. The difference between the qualities of these bacteria is reflected on the sequence of chromosomes controlling this genetic information, and characteristic sequence is present every bacterium.

For example, it is shown that 16S rDNA coding 16S rRNA subunits of ribosomal RNA of bacteria varies between the bacteria and the bacteria can be identified by this difference in sequence (Christine et al., Appl. Environ. Microbiol. 65: 102–109).

DISCLOSURE OF THE INVENTION

An object of the present invention is to analyze an intestinal bacterial flora through difference in nucleic acid sequence between intestinal bacteria.

A method of analyzing an intestinal bacterial flora of a subject according to an aspect of the present invention comprises a nucleic acid amplifying step of amplifying nucleic acid of an intestinal bacterial group in a sample extracted from the subject with a specific PCR primer and an analyzing step of analyzing the intestinal bacterial flora on the basis of an amplified fragment obtained in the nucleic acid amplifying step.

The analyzing step may include a fractionating step of fractionating the amplified fragment by electrophoresis and an analyzing step of analyzing a fractional pattern obtained in the fractionating step.

The analyzing step may include performing hybridization with the amplified fragment using a plurality of probes so that analysis of the intestinal bacterial flora is performed from presence/absence of formation thereof.

The probes may be arranged on specific positions in a detector.

Nucleic acid amplified from each intestinal bacterium with the PCR primer employed in the nucleic acid amplifying step may be used as a probe.

The nucleic acid obtained in the nucleic acid amplifying step may be denatured before introduction into the detector.

A set temperature of the detector may be arbitrarily changeable according to an instruction from a temperature controller.

The specific PCR primer may have a sequence capable of amplifying a nucleic acid region coding 16S rRNA of the intestinal bacterium.

The specific primer may be a primer having a specific amplification probability.

An apparatus for analyzing an intestinal bacterial flora according to another aspect of the present invention comprises a nucleic acid amplifier that amplifies nucleic acid of an intestinal bacterial group in a sample extracted from a subject, an electrophoretic unit that fractionates the amplified nucleic acid by electrophoresis, and an analyzer that analyzes the intestinal bacterial flora from an electrophoretic pattern fractionated in the electrophoretic unit.

An apparatus for analyzing an intestinal bacterial flora according to still another aspect of the present invention comprises a nucleic acid amplifier that amplifies nucleic acid of an intestinal bacterial group in a sample extracted from a subject, a hybridizer that hybridizes the amplified nucleic acid and a specific probe, and an analyzer that analyzes the intestinal bacterial flora from a result of the hybridization.

The hybridizer may include a DNA chip where a probe formed by nucleic acid derived from the intestinal bacterial group is arranged.

The hybridizer may include a detector where a specific probe formed by nucleic acid derived from the intestinal bacterial group is arranged on a specific position.

Nucleic acid amplified from each intestinal bacterium with a PCR primer employed in the nucleic acid amplifier may be used as a probe.

A DNA denaturation part that denatures nucleic acid may be provided on a front stage of the detector.

A temperature controller capable of arbitrarily changing a set temperature of the detector may be provided.

According to the present invention, as hereinabove described, an intestinal bacterial group is detected on the basis of chromosomes of the intestinal bacterial group, so that the intestinal bacterial flora can be analyzed without performing cultivation corresponding to every intestinal bacterium dissimilarly to the conventional art. Therefore, analysis of the intestinal bacterial flora becomes easy, and it is possible to perform health management or the like on the basis of change or the like of the intestinal bacterial flora.

The invention can also be utilized for identification of intestinal bacteria concerning a physical state such as affection or senescence.

According to the present invention, nucleic acid of intestinal bacteria is amplified by the specific PCR primer and the intestinal bacterial flora is analyzed from a genetic technique on the basis of the amplified fragment thereof, so that a plurality of intestinal bacteria can be detected through the same operation without performing a complicated cultivating operation corresponding to cultivation conditions for each intestinal bacterium dissimilarly to the conventional art.

The analyzing step can include a fractionating step of fractionating the amplified fragment by electrophoresis and an analyzing step of analyzing the fractional pattern obtained in the fractionating step. Alternatively, it is also possible to make hybridization with the amplified fragment with a specific probe group for performing analysis of the intestinal bacterial flora from presence/absence of hybridization thereof.

It is known that nucleic acid coding 16S rRNA (hereinafter referred to as 16S rDNA) slightly varies with the bacterium (Christine et al., cited above), and hence it is possible to investigate the distributed state of bacteria in the intestine (i.e., the intestinal bacterial flora) by amplifying this DNA as an object and analyzing the amplified fragment thereof according to the present invention.

According to the present invention, it is possible to simply amplify nucleic acid of an intestinal bacterium in a sample by employing one or more types of primers having a specific amplification probability. The specific amplification probability means such a one that the primer can arbitrarily amplify template nucleic acid, and the number of amplified fragments in this case is specified to some extent with respect to the sequence length of the template nucleic acid.

According to the present invention, nucleic acid of intestinal bacteria is amplified by the specific primer in the nucleic acid amplifier, the amplified nucleic acid is fractionated in a fractionating part, and analysis of the intestinal bacterial flora is performed in the analyzer on the basis of this fractional pattern. Therefore, it is possible to analyze the intestinal bacterial flora in a relatively short time on the basis of the nucleic acid of the intestinal bacteria without performing a complicated cultivating operation corresponding to cultivating conditions for each intestinal bacterium dissimilarly to the conventional art.

According to the present invention, the intestinal bacterial flora can be analyzed by hybridization in place of electrophoresis, whereby it is possible to improve specificity and improve throughput according to dot hybridization or the like.

Because a large number of probes are integrated on a substrate of a DNA chip, hybridization analysis employing the large number of probes can be performed in parallel, and further improvement of the throughput is attained.

BRIEF DESCRIPTION OF THE DRAWINGS

FIG. 4 is a block diagram of a system for analyzing an intestinal bacterial flora according to a third embodiment.

FIG. 5 is a block diagram of a system for analyzing an intestinal bacterial flora according to a fourth embodiment.

BEST MODES FOR CARRYING OUT THE INVENTION

Preferable embodiments of the present invention are now described with reference to the drawings.

[First Embodiment]

Figure 1:
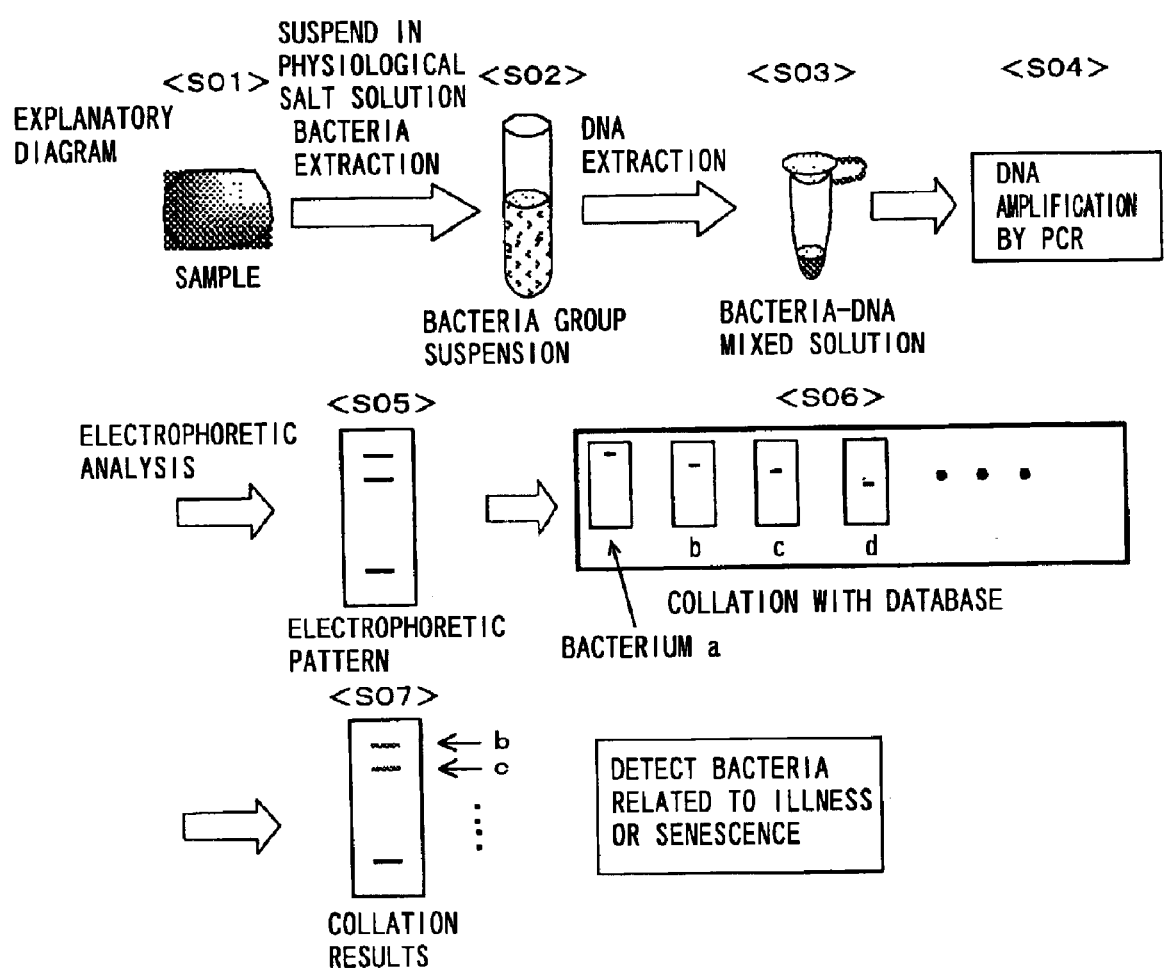
FIG. 1 is a diagram typically showing operations in a method for analyzing an intestinal bacterial flora according to a first embodiment.

FIG. 1 typically shows a process diagram of a method for analyzing an intestinal bacterial flora according to a first embodiment.

(1) Preparation of Sample

Referring to FIG. 1, a sample such as dejection, for example is extracted, from a subject (S01), and this sample is suspended in a physiological salt solution or the like. This suspension is thereafter passed through a filter or the like so that solids such as unnecessary cells other than bacteria are removed and a bacterial group suspension is prepared (S02).

The filter employed for this separation/recovery of bacteria is not particularly restricted so far as the same has a size capable of separating the bacteria from other individuals. Preferably, a plurality of filters having different diameters are employed as a filter and the suspension is passed through a filter of loose texture to filters of fine textured successively, so that clogging of the filters can be reduced. For example, it is also possible to preferably utilize a stoma filter (Gunze Sangyo, Ltd.) as the filter of loose texture in combination with membrane filters such as polypropylene screens of 80 $\mu$m, 45 $\mu$m and 25 $\mu$m (MILLIPORE), Mini Sarto of 5 $\mu$m (sartorius) and the like as the filters of fine texture.

(2) Amplification with PCR of Specific DNA

The said separated bacteria are recovered as a bacterial suspension, and DNA extraction is performed with this (S03). This DNA extraction is executed according to current protocol in molecular biology, p. 2.4.1–2.4.5 (Green Publishing Associates and Wiley-Interscene, New York), for example, and the extracted DNA is finally suspended in a buffer solution (e.g., a Tris-HC1 buffer solution or the like) so that this nucleic acid suspension is prepared.

More specifically, the bacterial suspension is injected into a microtube or the like, for example, and centrifuged. After the centrifugation, a supernatant is removed and an obtained pellet is re-suspended in a TE buffer containing SDS and proteinase K or the like. The re-suspension is incubated at 37° C. for one hour so that bacteriolysis is performed. After the incubation, a 5 M sodium chloride solution is added to the suspension and mixed. After the mixing, a CTAB (hexadecyl trimethyl ammonium bromide)/sodium chloride solution is added and incubated at 65° C. for 10 minutes.

After addition of a chloroform/isoamyl alcohol solution by the same quantity, centrifugation is performed for five minutes for sedimenting bacterial bodies. An obtained supernatant is transferred to another tube or the like, phenol/chloroform/isoamyl alcohol is added, centrifugation is made and the supernatant is recovered for deproteinization.

The recovered supernatant is transferred to still another tube, and isopropanol is added so that nucleic acid is sedimented. The sedimented nucleic acid is washed with 70% ethanol, the supernatant is removed, and the sediment is lightly dried. This sediment is re-suspended with a TE buffer into the nucleic acid suspension.

PCR is executed with the prepared nucleic acid suspension (S04). As the nucleic acid amplified in this PCR, a region where sequence differs between bacteria and the bacteria can be identified on the basis of the sequence, e.g., 16S rDNA of the bacteria or the like can be listed.

The 16S rDNA slightly differs in sequence between bacteria and a genealogical tree based on the sequence or the like is also created (Christine et al., cited above), and hence the bacteria can be also specified in a later analyzing step based on this 16S rDNA.

Therefore, the PCR primer employed here may be that capable of amplifying the specific region selected in the above, and a pair of primers having sequence numbers 1 and 2 or a pair of primers having sequence numbers 1 and 3 can be preferably employed as primers capable of amplifying the said 16S rRNA, for example. A pair of primers having sequence numbers 4 and 5 can also be preferably employed as primers capable of amplifying 16S rRNA (Microbes and Environments 12:57–68). Further, a pair of primers having sequence numbers 6 and 7 may be employed ("Intestinal Flora and Intestinal Proliferation", Proceedings of 3rd Symposium on Intestinal Flora, Tokyo, 1994, Japan Scientific Societies Press).

A PCR reaction liquid can be prepared according to the said Christine et al. (cited above), for example. More specifically, a buffer for PCR is added to part of the said nucleic acid suspension and each enzyme is added so that final concentrations are 3 mM of magnesium chloride, 5% of DMSO, each 0.1 mM of dNTP and 0.5 U Taq of enzyme for preparing the reaction liquid.

As to reaction conditions for PCR, the template DNA is sufficiently denatured by maintaining a temperature of 94° C. for seven minutes, thereafter three steps of a denaturing step (94° C. for one minute), an annealing step (54° C. for one minute) and an extension step (72° C. for one minute) are repeated by 35 cycles and finally the extension step is executed while maintaining a temperature of 72° C. for 10 minutes.

(3) Fractionation of Amplified Fragment by Electrophoresis

Electrophoresis is executed with part of the said PCR reaction liquid (S05) to fractionate amplified fragments. As this electrophoresis, electrophoresis using a general acrylamide gel or an agarose gel may be employed, it is preferable to utilize temperature gradient electrophoresis when amplified fragments slightly different in base sequence similarly to the said 16S rDNA are included in plural in the reaction liquid and in order to make it possible to identify these amplified fragments.

In this gradient electrophoresis, a 6% acrylamide gel containing 8 M of urea and 20% of formamide is prepared and the gel is previously made to form a temperature gradient of 39 to 52° C. The said PCR reaction liquid is loaded on this gel, and electrophoresis at 100 V for 17 hours is performed in the state formed with the temperature gradient from 39° C. to 52° C.

Finally, a electrophoretic (fractional) pattern after electrophoresis is visualized by ethidium bromide dyeing or the like and is read by a computer and the following analysis of the intestinal bacterial flora is performed on the basis of this fractional pattern.

(4) Analysis of Intestinal Bacteria

For analysis of the said fractional pattern, for example, 16S rDNA of each intestinal bacterium is fractionated under conditions same as the above and the fractional pattern is recorded in a database. The fractional pattern of the said subject is contrasted with the data on this database (S06), and the types of bacteria included in the intestinal bacterial flora can be also identified directly (S07). When bacteria related to illness or senescence are previously identified at this time, presence/absence of the bacteria may be determined.

Alternatively, when the relation between each intestinal bacterium and the amplified fragments is not associated, periodically measured fractional patterns showing the intestinal bacterial flora of the subject are recorded in the database so that change of the intestinal bacterial flora can also detected in contrast with the fractional patterns on the database. It is also possible to investigate intestinal bacteria relevant to affection or bad condition on the basis of new amplified fragments detected here or the like.

(5) Application

Figure 2:
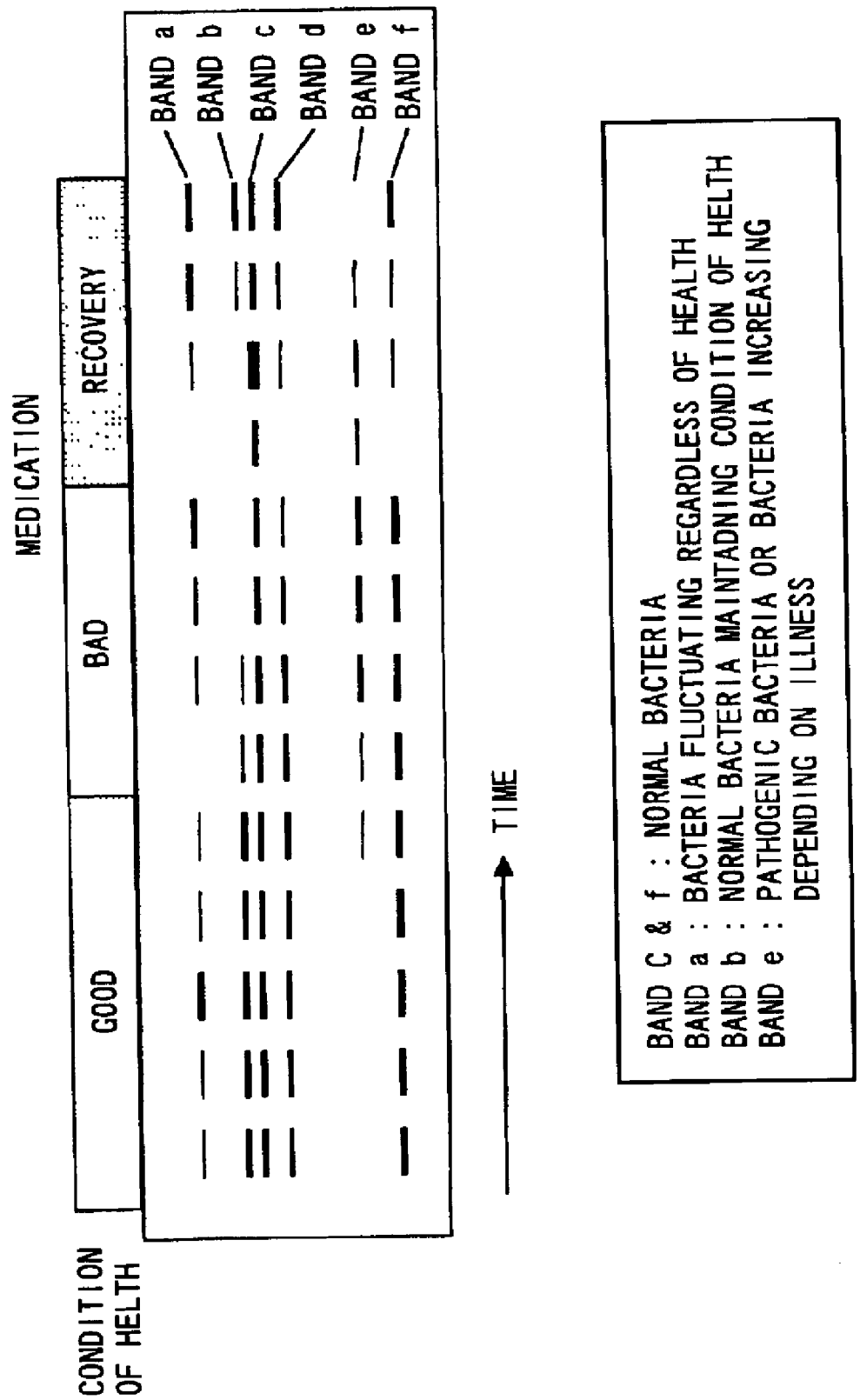
FIG. 2 is a diagram typically showing results of analysis of the intestinal bacterial flora according to the first embodiment.

FIG. 2 shows a case of monitoring the condition of health of a single subject on the basis of an intestinal bacterial flora as exemplary application of the present method for analyzing an intestinal bacterial flora.

The intestinal bacterial flora of the subject is periodically investigated through the aforementioned series of operations, and a fractional pattern of amplified fragments of 16S rDNA or the like of an intestinal bacterial group in good condition of health are recorded. Also when the subject feels bad condition in the body, fractional patterns of 16S rDNA in the intestinal bacterial group are similarly continuously investigated through the aforementioned series of operations. This fractional patterns "at the time of bad condition" and the said fractional patterns "at the time of good condition" are compared, and presence/absence of a band appearing or disappearing at the time of bad condition and change etc. of the intensity of the band are determined.

Analysis of the intestinal bacterial flora is continuously performed also in a period when the physical condition recovers. Whether or not the band appearing at the time of bad condition disappears, or whether a band characterized at the time of a good condition or the like appears or band intensity rises is monitored.

Explaining with reference to FIG. 2, for example, it is shown that a band e appears at the time of bad condition or immediately before entering bad condition while a band b appears when entering bad condition, and band intensity rises as this bad condition state continues. "At the time of recovery", the band e disappears again and the band b characterized at the time of a good condition substitutionally appears. Thus, it becomes possible to detect change of the physical condition by detecting characteristic fractional pattern change of the intestinal bacterial group following physical condition change.

Thus, it is considered that the intestinal bacterial flora varies with the condition of health, stress etc., and hence this analysis of the intestinal bacterial flora is expected to be utilized for health examination or the like as means capable of detecting fine change of the condition of health undetectable from a blood test or the like. In particular, the intestinal bacterial flora also varies with a mental factor such as stress, and hence it is also expected to be utilized for an operation of detecting influence on the body resulting from the mental factor in an early stage.

A band pattern derived from intestinal bacteria showing the condition of health can be specified from the said results of determination shown in FIG. 2, while intestinal bacteria related to the bad condition time can be also identified from amplified bands appearing at the time of the bad condition. Further, it is possible to apply the analysis to study on influence of such intestinal bacteria on the human body or the like.

As shown in FIG. 2, further, this method for analyzing an intestinal bacterial flora can be utilized also for, when administering a medicine or the like, investigating influence to the intestinal bacterial flora exerted by the medicine.

[Second Embodiment]

While the said first embodiment has shown a method of detecting a bacterial group with indication of a specific region of intestinal bacteria and analyzing a bacterial flora, the present embodiment shows a method of detecting a bacterial group with objects of arbitrary regions of chromosomes and analyzing an intestinal bacterial flora.

Also in the second embodiment, a point of preparing a bacterial suspension from a sample extracted from a subject and a point of preparing a nucleic acid suspension from the prepared bacterial suspension are similar, and hence description thereof is omitted here.

(1) PCR Amplification of Arbitrary Region of Intestinal Bacterial Group

In the second embodiment, amplified fragments are synthesized with objects of arbitrary regions of chromosomes and a bacterial group is detected on the basis of these synthesized amplified fragments. While there is a primer of random PCR or the like as a primer capable of amplifying arbitrary regions of such various bacteria, an extremely large number of amplified fragments are synthesized with a general random PCR primer, and when fractionated by electrophoresis, bands may be close so that pattern reading may be difficult. Therefore, arbitrary DNA fragments of the intestinal bacterial group are amplified using a primer having a specific amplification probability.

This primer having a specific amplification probability means a primer capable of amplifying a limited number of types of DNA fragments with respect to the base length of the said prescribed template nucleic acid. Reading of fractional patterns can be simplified in subsequent electrophoresis by thus using the primer capable of synthesizing specific amplified fragments.

Specifically, the amplification probability of the primer usable here is not particularly restricted, while the number of the amplified fragments is not more than 25 so that the amplified DNA fragments can be fractionated by electrophoresis and accurately analyzed, and the number of the amplified fragments is preferably set to at least about 10 in order to efficiently analyze a large number of intestinal bacterial groups.

On the other hand, it is assumed that the chromosome length of the bacteria is $8 \times 10^5$ to $1 \times 10^7$ bp (Molecular Biology of the Cell, third edition, p. 340), and chromogenes of the intestinal bacterial group are $5 \times 10^6$ bp on the average. It is considered that about 100 types of intestinal bacteria are present, and hence the base length is assumed to be $5 \times 10^8$ bp as the overall intestinal bacterial group. When employing a primer having an amplification probability capable of synthesizing a single amplified fragment per $5 \times 10^7$ bp with respect to such a template, about 10 types of amplified bands are formed, and it is possible to investigate 10 types of bacteria when the amplified bands are derived from different bacteria.

According to the said calculation, therefore, it is necessary to employ at least 10 types of primers having the amplification probability of $5 \times 10^{-7}$, for example, in order to investigate 100 types of intestinal bacteria. Considering deviation of base sequence depending on bacteria, it is preferable to employ about 50 types of primers having the amplification probability of $5 \times 10^{-7}$, more reliably about 100 types of primers.

This amplification probability of the primers is an example, and the amplification probability is not restricted to $5 \times 10^{-7}$. Therefore, it is possible to select a desired amplification probability by an experimental operation or the like and increase or decrease the number of types of primers in correspondence thereto.

In order to find this amplification probability, a solution where a large number of types of nucleic acids are mixed such as a nucleic acid suspension containing a plurality of nucleic acids derived from intestinal bacteria, for example, is employed as a template with various primes and the number of amplified fragments produced with the respective primers are investigated. The amplification probability of each primer is found from results of this investigation, and primers having a desired amplification probability are selected from the primers. As candidates for primers employable for this investigation, 5'-GGCTTCGAATCG-3' (sequence number 8), 5'-TGGATCTTTGAC-3' (sequence number 9), 5'-AACATCTCCGGG-3' (sequence number 10) etc. according to Inoue et al. ("Study of Population Dynamics by SSC-PCR Method", Lectures of Second Symposium of Japan Society of Water Environment (1999), p. 54 to 55, Japan Society of Water Environment) and DNA oligomer (by Nippon Gene Co., Ltd.) or the like as a commercially available primer can be employed.

(2) Conditions of PCR

The composition of the PCR reaction solution can contain 1×PCR buffer, 1.5 mM of $MgCl_2$, 200 $\mu$M of dNTPmix, 2 $\mu$M of primers, 0.0125 units/$\mu$L of Taq polymerase. The nucleic acid suspension in the said first embodiment can be employed for the template DNA.

The PCR reaction conditions can be set to 94° C. for one minute, 45° C. for two minutes and 72° C. for three minutes, and the reaction cycle in this case can be set to 35 cycles, for example. However, these conditions etc. are illustrative, and hence it is possible to change these conditions.

(3) Method of Amplifying DNA Fragment and Analysis by Electrophoresis

For example, a primer having a different amplification probability, e.g., a primer having an amplification probability of $5 \times 10^{-7}$ is added to each well of a microtiter plate, and mixed with the said nucleic acid suspension. A PCR buffer, magnesium chloride, a dNTP mix and Taq polymerase are added as shown in Table 1, for preparing the reaction liquid.

TABLE 1

| Buffer | Final Concentration |
|---|---|
| Tris-HCl (pH8.3) | 10 mM |
| KCl | 50 mM |
| $MgCl_2$ | 1.5 mM |
| dNTPmix | 200 $\mu$M |
| Primer | 2 $\mu$M |
| Chromosome DNA | 10 pg/$\mu$L |
| Tag DNA Polimerase | 0.025 u/$\mu$L |

After the reaction liquid is prepared, it is set in a PCR amplifier, and PCR is executed under the aforementioned reaction conditions. This amplifier is not particularly restricted but a commercially available amplifier can be used in general.

After expiration of amplification reaction, part of the reaction liquid is subjected to electrophoresis, and amplified fragments are fractionated. As to conditions etc. of this electrophoresis, proper ones are used depending on the number and lengths of DNA fragments to be analyzed. For example, electrophoresis using an agarose gel, polyacrylamide gel electrophoresis or the like can be employed. When the lengths of the DNA fragments to be fractionated vary, a long range type gel and an apparatus can be employed.

After the electrophoresis, fractional patterns of the amplified fragments are visualized by ethidium bromide dyeing of the gel or the like or are read with a computer or the like. Finally, the subsequent general intestinal bacterial flora of the subject is analyzed as follows on the basis of these fractional patterns.

(4) Analysis of Intestinal Bacterial Flora on the Basis of Fractional Pattern

Figure 3:
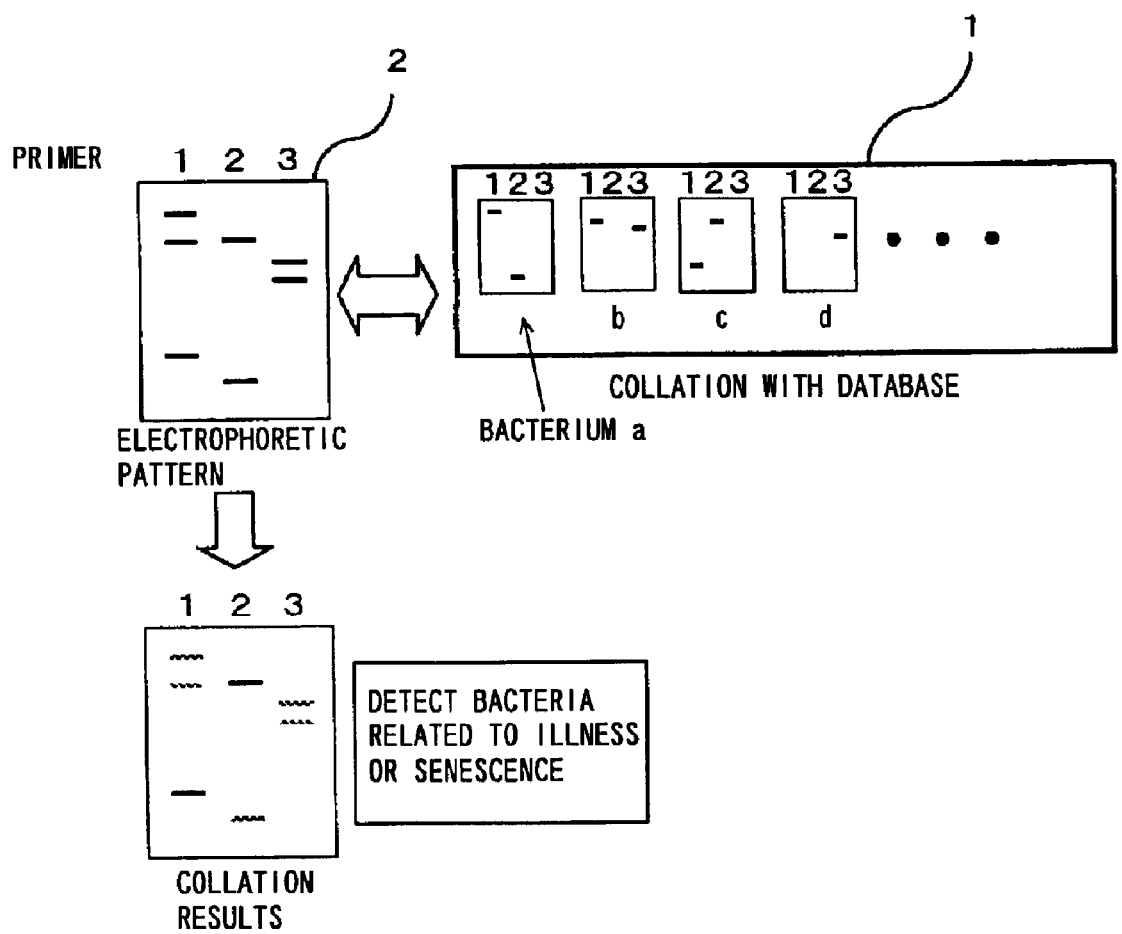
FIG. 3 is a diagram typically showing collation between a electrophoretic pattern of a subject and pattern data in a database in analysis of an intestinal bacterial flora according to a second embodiment.

For analysis of the intestinal bacterial flora, the chromosome of each intestinal bacterium is amplified under the same PCR condition employing the same primers used for the said analysis and electrophoretic patterns of the amplified fragments recorded in a database 1 are prepared as shown in FIG. 3, if possible.

An electrophoretic pattern 2 obtained from the sample of the subject is collated with the patterns in this database 1, for identifying the bacteria and analyzing the intestinal bacterial flora.

Alternatively, for analysis of the intestinal bacterial flora, it is preferable to previously periodically record and preserve fractional patterns showing the state of the intestinal bacterial flora of the subject also when the database recording the fractional pattern of each intestinal bacterium cannot be prepared as shown in FIG. 3. It is also possible to monitor the condition of health by contrasting the electrophoretic pattern with the recorded fractional patterns of the intestinal bacterial group and analyzing whether the electrophoretic pattern matches with a fractional pattern at the time when the condition of health is good or it does not match with the fractional pattern at the time of good condition but change takes place in the intestinal bacterial flora.

Thus, also in this embodiment, as a result of this analysis, intestinal bacteria readily propagating or decreasing at the time of bad condition may be identified from characteristic amplified band appearing at the time of bad condition, and it is also possible to investigate a state to the intestinal bacterial group supplied at the time of medication with this second embodiment.

While the case of fractionating amplified fragments by electrophoresis and analyzing the intestinal bacterial flora from the fractional patterns in the aforementioned first or second embodiment, hybridization may be employed in place of this. In this case, for the probes, probes capable of performing classification or the like of the intestinal bacterial group can be employed. For example, it is possible to employ a probe group having a characteristic region of 16S rDNA derived from each intestinal bacterium in the first embodiment, and a probe group having sequence complementary to fragments amplifiable by a primer having a specific amplification probability in the second embodiment. These probe groups and each amplified fragment may be hybridized and each amplified fragment and the type of the intestinal bacterium may be associated for analyzing the intestinal bacterial flora on the basis of presence/absence of hybridization.

The throughput can be improved according to dot plot hybridization in particular, and further improvement of the throughput is attained by employing a DNA chip described later.

In hybridization analysis employing these dot plot hybridization and DNA chip, it is desirable that the types of the bacteria forming the intestinal bacterial flora can be specified from presence/absence of hybridization on a specific dot or a section of a specific chip, while change of the intestinal bacterial flora may be detected from pattern change of hybridization of the DNA chip or the like even when the types of the bacteria cannot be specified. From this analysis, intestinal bacteria relevant to "bad condition time" or the like may be specified with a probe on a dot or a section where a signal appears at the time of bad condition etc. of the subject.

[Third Embodiment]

In this embodiment, a system structure capable of executing the method for analyzing an intestinal bacterial flora according to the said first or second embodiment is described with reference to FIG. 4.

Referring to FIG. 4, an automatic bacteria extractor 12 extracting bacteria from a sample such as dejection extracted from a subject is provided in a system 10. A physiological salt solution is stored in this automatic bacteria extractor 12, and the sample is suspended in this physiological salt solution. In order to remove solids other than bacteria from a prepared suspension, a filter is provided in this automatic bacteria extractor 12, which separates only the bacteria through this filter to prepare a bacterial suspension. In order to prevent clogging of the filter at the time of recovery of the bacteria, this filter preferably comprises a filter of loose texture and filters of fine texture. For example, it is also possible to preferably utilize a stoma filter (Gunze Sangyo, Ltd.) as the filter of loose texture in combination with membrane filters such as polypropylene screens of 80 $\mu$m, 45 $\mu$m and 25 $\mu$m (MILLIPORE), Mini Sarto of 5 $\mu$m (sartorius) and the like as the filters of fine texture.

To the said automatic bacteria extractor 12, an automatic DNA extractor 14 is connected through a transfer line 13 transferring the bacterial suspension prepared in this automatic bacteria extractor 12. A reagent or the like for extracting DNA from the bacteria is provided in this automatic DNA extractor 14, DNA is extracted from the bacteria, so that a DNA suspension is prepared. A commercially available automatic DNA extractor or the like may be utilized for this automatic DNA extractor.

A PCR reactor 16 is connected to the said automatic DNA extractor 14 through a transfer line 15 for transferring the prepared DNA suspension, and preparation of a PCR reaction liquid and PCR reaction are executed in this PCR reactor 16. Therefore, PCR primers for analyzing the intestinal bacterial flora and a reagent (a buffer liquid, dNTP, polymerase, salt such as magnesium chloride or the like) for preparing another PCR reaction liquid are stored in this PCR reactor 16, and the reagent is added to the DNA suspension transferred through the transfer line 15 so that the PCR reaction liquid is prepared. After this preparation of the PCR reaction liquid, PCR reaction is executed under desired conditions of an operator.

The primers in this PCR reactor 16 can be selected in correspondence to an object amplified region regarded. When amplifying 16S rDNA as a specific region of an intestinal bacterium as shown in the first embodiment, for example, a pair of primers having sequence numbers 1 and 2, a pair of primers having sequence numbers 1 and 3 or a pair of primers having sequence numbers 4 and 5 can be selected. When performing DNA amplification directed to an arbitrary region of an intestinal bacterium, the primers having the desired amplification probability in the second embodiment can be employed.

An electrophoretic unit 18 is connected to the PCR reactor 16, and the reaction liquid in the PCR reactor 16 is electrophoresed in an electrophoretic gel in the electroophoretic unit 18 so that fractions amplified fragments in the reaction liquid are fractionated. This PCR reactor 16 and the electrophoretic unit 18 can be connected with each other through a plurality of capillaries 17. Forward ends of these capillaries 17 can be structured to be connected to respective lanes of an electrophoretic gel (not shown) in the electrophoretic unit 18 so that each PCR reaction liquid is injected into each lane of the electrophoretic gel.

An analyzing computer 20 is connected to the said electrophoretic unit 18 through a signal line 19. This analyzing computer 20 reads the fractional patterns fractionated in the electrophoretic unit 18, and the fractional patterns read here are analyzed.

For this analysis of the fractional patterns, a database 22 is connected to the analyzing computer 20. For example, fractional pattern data with respect to a specific region of 16S rDNA derived from each intestinal bacterium or the like, fractional pattern data of each bacterium in a case of employing the primers having a specific amplification probability shown in the second embodiment, fractional pattern data in a periodic test of the subject and the like are recorded in this database.

These fractional patterns on the database and the fractional patterns obtained from the electrophoretic unit 18 are contrated with each other in the analyzing computer 20, analysis of the intestinal bacterial flora is performed, intestinal bacteria is specified and whether or not there is change in the intestinal bacterial flora or whether the intestinal bacteria flora matches with an intestinal bacterial flora "at the time of good condition" or "at the time of bad condition" etc. is determined.

In order to make display or the like of finally determined results, the analyzing computer 20 is connected to a display 24, and display and output of the determined results are performed in this display.

Thus in this system, the method for analyzing an intestinal bacterial flora shown in the said first embodiment or the second embodiment is executed, and the intestinal bacterial flora is analyzed on the basis of nucleic acid of an intestinal bacterial group extracted from the subject. In this system, therefore, labor of making cultivation in correspondence to each intestinal bacterium and a cultivation time can be reduced dissimilarly to the conventional art.

[Fourth Embodiment]

A fourth embodiment shows another system 25 for analyzing an intestinal bacterial flora. While the system of the said third embodiment includes the electrophoretic unit 18 and fractionates the amplified fragments by electrophoresis, a hybrid analyzer 26, for example, in place of the said electrophoretic unit 18 may be provided, as substitution for this fractionating step by electrophoresis, as shown in FIG. 5.

This hybrid analyzer 26 includes a DNA chip or the like, for example, and a DNA region derived from each intestinal bacterium which can be amplified by a primer employed for analysis of the intestinal bacterial flora, e.g., a 16S rDNA region or a DNA region which can be amplified by a primer having a desired amplification probability is independently fixed to this DNA chip or the like. Fragments amplified in the said PCR reactor 16 are denatured and thereafter brought into contact with this DNA chip or the like, for hybridization.

Fabrication etc. of this DNA chip can be executed according to Information Processing, vol. 40 (March 1990), pp. 323–325. As to fabrication of the DNA chip, for example, either a probe arrangement type such that a previously prepared probe is arranged on a chip substrate, e.g., a GEM array (by Synteni) or a probe synthesis type such that probe DNA is produced by directly employing extension reaction of DNA on a substrate of glass or silicon, e.g., GeneChip (by Affymetrix) may be available. Simply, a commercially available DNA chip fabricating apparatus and a DNA chip reader (by GMS, for example) for reading thereof or the like may be employed.

When thus employing the DNA chip, on the other hand, the position on the DNA chip etc. of each intestinal bacterium are recorded in a database 30. In the analyzing computer 28, the intestinal bacterial group is specified from the position where hybridization is made on the DNA chip on the basis of data in the database 30, the intestinal bacterial flora is analyzed and results of analysis are displayed on a display 32.

Alternatively, when the types of the bacteria forming the intestinal bacterial flora cannot be specified from presence/absence of hybridization, it is also possible to detect change of the intestinal bacterial flora on the basis of pattern change of hybridization on the DNA chip between "good condition" and "bad condition" as to the condition of health. Intestinal bacteria relevant to "bad condition" or the like may be specified from results of this analysis with a probe on a section where hybridization is observed at the time of bad condition of the subject or the like.

Thus, the hybrid analyzer 26 is provided in place of the electrophoretic unit and bacteria can be identified based upon presence/absence of hybridization, so that operations are more simplified.

Figure 6:
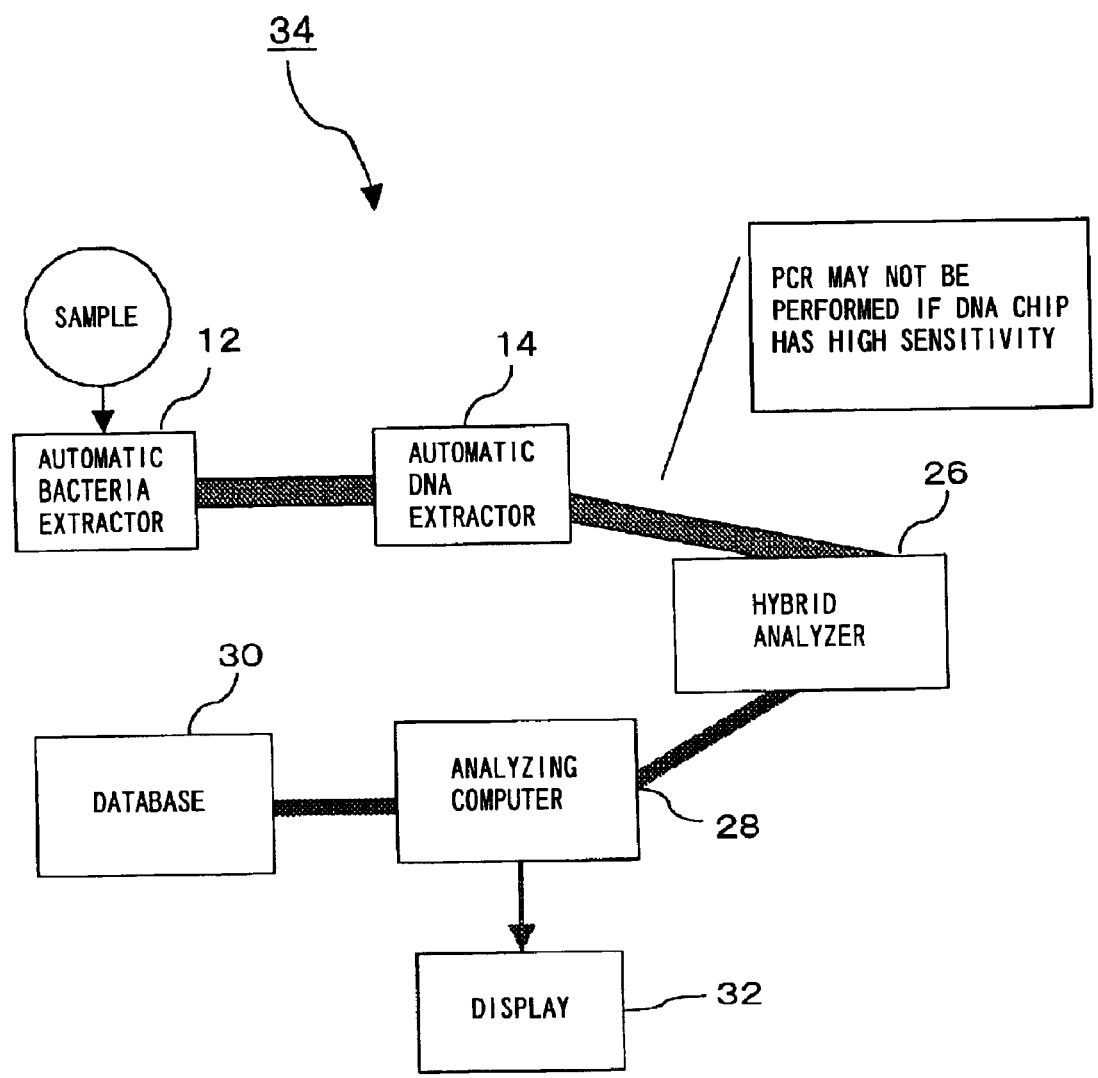
FIG. 6 is a block diagram of another system for analyzing an intestinal bacterial flora according to the fourth embodiment.

When a nucleic acid suspension prepared from the bacterial suspension contains DNA of a quantity necessary for analysis of the intestinal bacterial flora with the DNA chip or the like, the system may be structured by omitting the said PCR reactor and directly connecting the automatic DNA extractor 14 and the hybrid analyzer 26 as in a system 34 shown in FIG. 6.

[Fifth Embodiment]

A fifth embodiment shows still another system 40 for analyzing an intestinal bacterial flora.

A system structure capable of executing a method for analyzing an intestinal bacterial flora according to the fifth embodiment is described with reference to FIG. 7.

Figure 7:
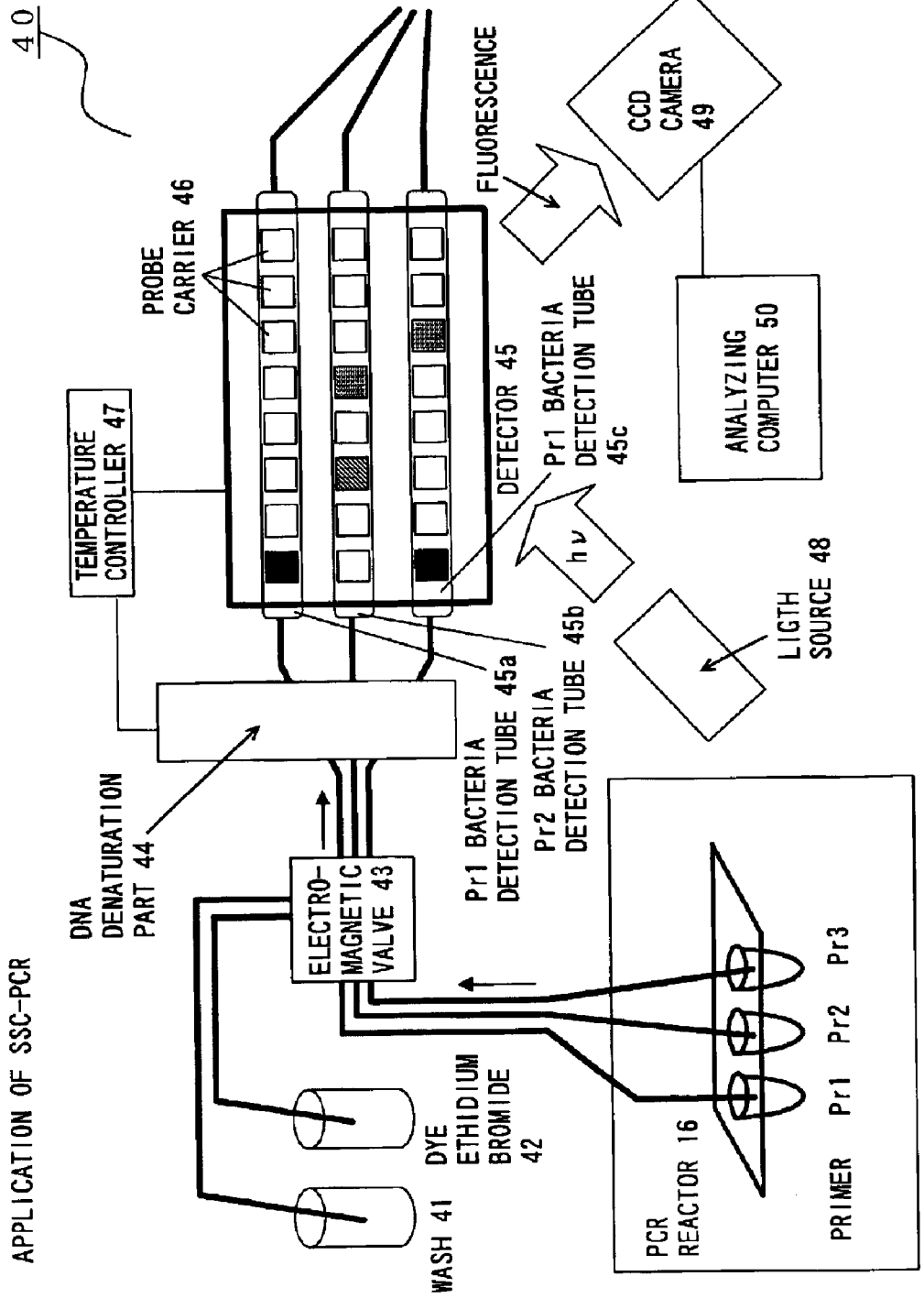
FIG. 7 is a block diagram of a system for analyzing an intestinal bacterial flora according to a fifth embodiment.

Referring to FIG. 7, a PCR reactor 16 is connected to an electromagnetic valve 43, a DNA denaturation part 44 and a detector 45 through tubes, and so structured that a reaction liquid in the PCR reactor 16 is finally discharged from a discharge port to the exterior of the system 40. The electromagnetic valve 42 is provided between the PCR reactor 16 and the DNA denaturation part 44, and a wash 41 or a dye (pigment) (e.g., ethidium bromide) can be fed to the detector 45 (described later) by switching this electromagnetic valve 43.

The detector 45 comprises a bacteria detection tube 45a for Pr1, a bacteria detection tube 45b for Pr2 and a bacteria detection tube 45c for Pr3, and DNA regions derived from respective intestinal bacteria which can be amplified by a primer employed for analysis of the intestinal bacterial flora, such as 16S rDNA regions and DNA regions which can be amplified by a primer having a desired amplification probability, for example, are independently fixed to probe carriers of the respective detection tubes 45a to 45c.

While various techniques such as:

(1) a technique employing filters for the probe carriers heat-treating probe carriers formed by nitrocellulose films (filters) to a prescribed temperature or irradiating probe carriers formed by nylon membranes with ultraviolet rays, (2) a chemical bonding technique bonding probe carriers and probes through thiol molecules or the like, and (3) a biotinylation technique employing biotin, have been established as techniques of this fixation of DNA regions to probe carriers, the present invention is not restricted to these techniques.

A temperature controller 47 can arbitrarily set the temperatures of the DNA denaturation part 44 and the detector 45. It is possible to control the denaturation ratio of DNA in the DNA denaturation part 44 and the ratio of a hybridization state in the detector 45 due to this temperature control.

A light source 48 irradiates the detector 45 with visible light or ultraviolet light, while a CCD camera 49 captures the hybridization state in the detector 45 as the light intensity of fluorescence or light emission, feeds optical data thereof to a rear-stage analyzing computer 50, and intestinal bacteria is detected in this analyzing computer 50 for identifying the same.

In order to capture the hybridization state in the detector 45 as the light intensity of fluorescence, light emission or the like, the following techniques are preferably employed:

(1) fluorescent dye modification of primer employing a primer modified with a dye on DNA, (2) dyeing DNA double chained by hybridization with double chain DNA dyeing reagent, ethidium bromide, SYBR Green (reagent by Nippon Gene), (3) usage of DIG (BOEHRINGER MANNHEIM) and ECL (Amersham Pharmacia)

(4) usage of surface plasmon resonance and mass change measurement with a quartz resonator An analyzing method of the system 40 according to the fifth embodiment is now described with reference to a process diagram of FIG. 8.

Figure 8:
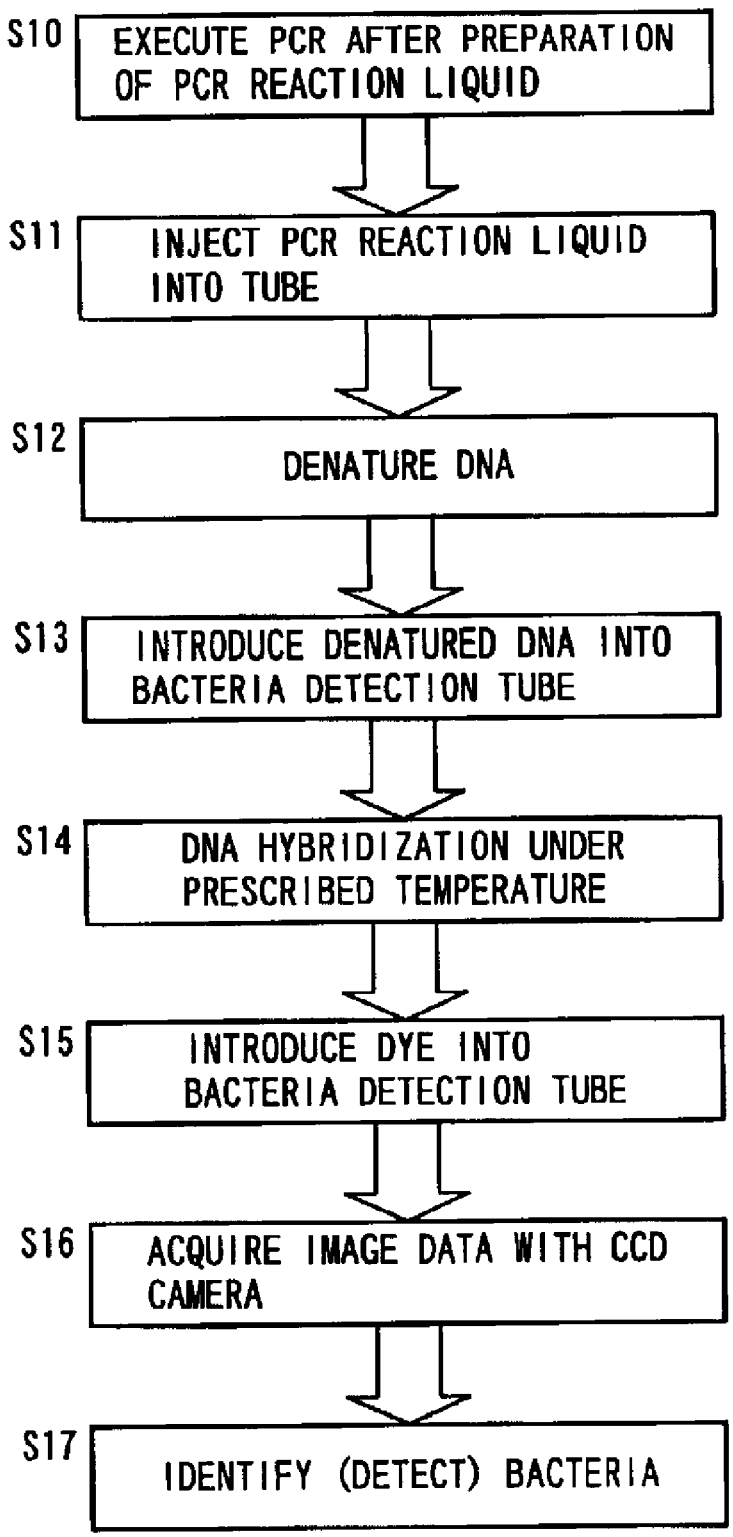
FIG. 8 is a process diagram of the system for analyzing an intestinal bacterial flora according to the fifth embodiment.

Referring to FIG. 8, PCR is executed under the PCR reaction conditions shown in the second embodiment (S10). In this embodiment, three types of primers were employed (Pr1, Pr2 and Pr3).

Thereafter the electromagnetic valve 43 is adjusted so that the PCR reaction liquid injected into the tubes flows into the DNA denaturation part 44 (S11).

In the DNA denaturation part 44, the temperature is raised to a prescribed temperature by the temperature control 47 to denature DNA (S12).

The denatured DNA is introduced into the Pr1 bacteria detection tube 45a, the Pr2 bacteria detection tube 45b and the Pr3 bacteria detection tube 45c communicating with each primer of the detector 45 through tubes (S13).

The temperature controller 47 sets the Pr1 bacteria detection tube 45a, the Pr2 bacteria detection tube 45b and the Pr3 bacteria detection tube 45c to a prescribed temperature, thereby rendering the denatured DNA in each detection tube readily hybridized (S14).

When employing fluorescent dye modification, ethidium bromide 42 is injected into the Pr1 bacteria detection tube 45a, the Pr2 bacteria detection tube 45b and the Pr3 bacteria detection tube 45c through the electromagnetic valve 43 (S15). Thus, when the probe carrier is irradiated with light from the light source 48, the denatured DNA fluoresces if hybridized, and the light intensity such as the degree of this fluorescence can be acquired with the CCD camera 49 as image data (S16).

The obtained image data is transmitted to the analyzing computer 50 and compared with set data of the probe carrier 46 to identify (detect) (S17).

While the example employing a dye has been mentioned in the step S15, it is not restricted to this but another technique capable of capturing the hybridization state of the detector 45 can be applied, and hence the processing of the step S15 may be omitted as the case may be.

When repetitively using the system 40, it is possible to release the temporarily hybridized DNA by adjusting the electromagnetic valve 43 to feed the wash 41, e.g., a sodium hydroxide solution to the detector 45. Alternatively, it is possible to enhance release of the hybridized DNA also by controlling the temperature of the detector 45 by the temperature controller 47.

What is claimed is:

1. A method for analyzing an intestinal bacterial flora of a subject, comprising:
    a nucleic acid amplifying step of amplifying nucleic acid of an intestinal bacterial group in a sample extracted from the subject with a specific PCR primer; and
    an analysis step of analyzing the intestinal bacterial flora on the basis of an amplified fragment obtained in said nucleic acid amplifying step, wherein
    hybridization with said amplified fragment is performed using a plurality of probes so that analysis of the intestinal bacterial flora is performed based upon presence/absence of formation thereof in said analyzing step, and
    said probes are arranged on specific positions in a detector.

2. The method for analyzing an intestinal bacterial flora according to claim 1, wherein said probes are arranged on specific positions in a detector.

3. The method for analyzing an intestinal bacterial flora according to claim 2 or 1, wherein nucleic acid amplified from each intestinal bacterium with the PCR primer employed in said nucleic acid amplifying step is used as a probe.

4. The method for analyzing an intestinal bacterial flora according to claim 2 or 1, wherein the nucleic acid obtained in said nucleic acid amplifying step is denatured before introduction into said detector.

5. The method for analyzing an intestinal bacterial flora according to claim 2 or 1, wherein a set temperature of said detector is arbitrarily changeable according to an instruction from a temperature controller.

6. The method for analyzing an intestinal flora according to any of claims 1 to 5, wherein said specific PCR primer has a sequence capable of amplifying a nucleic acid region coding 16SrRNA of said intestinal bacterium.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Synthesized DNA

<400> SEQUENCE: 1
agagtttgat cctggctcag                                       20

<210> SEQ ID NO 2
<211> LENGTH: 19
<212> TYPE: DNA
<213> ORGANISM: Artificial Sequence
<220> FEATURE:
<223> OTHER INFORMATION: Synthesized DNA

<400> SEQUENCE: 2

```
ggctaccttg ttacgactt                                              19

<210> SEQ ID NO 3
<211> LENGTH: 18
<212> TYPE: DNA
<213> ORGANISM: Artificial Sequence
<220> FEATURE:
<223> OTHER INFORMATION: Synthesized DNA

<400> SEQUENCE: 3
aaggaggtga tccaaccg                                               18

<210> SEQ ID NO 4
<211> LENGTH: 20
<212> TYPE: DNA
<213> ORGANISM: Artificial Sequence
<220> FEATURE:
<223> OTHER INFORMATION: Synthesized DNA

<400> SEQUENCE: 4
agagtttgat cctggctcag                                             20

<210> SEQ ID NO 5
<211> LENGTH: 19
<212> TYPE: DNA
<213> ORGANISM: Artificial Sequence
<220> FEATURE:
<223> OTHER INFORMATION: Synthesized DNA

<400> SEQUENCE: 5
ggctaccttg ttacgactt                                              19

<210> SEQ ID NO 6
<211> LENGTH: 32
<212> TYPE: DNA
<213> ORGANISM: Artificial Sequence
<220> FEATURE:
<223> OTHER INFORMATION: Synthesized DNA

<400> SEQUENCE: 6
gcggatcctg caggagtttg atcctggctc ag                               32

<210> SEQ ID NO 7
<211> LENGTH: 31
<212> TYPE: DNA
<213> ORGANISM: Artificial Sequence
<220> FEATURE:
<223> OTHER INFORMATION: Synthesized DNA

<400> SEQUENCE: 7
gcctcgagcg gccgctacct tgttacgact t                                31

<210> SEQ ID NO 8
<211> LENGTH: 12
<212> TYPE: DNA
<213> ORGANISM: Artificial Sequence
<220> FEATURE:
<223> OTHER INFORMATION: Synthesized DNA

<400> SEQUENCE: 8
ggcttcgaat cg                                                     12

<210> SEQ ID NO 9
<211> LENGTH: 12
<212> TYPE: DNA
<213> ORGANISM: Artificial Sequence
```

```
<220> FEATURE:
<223> OTHER INFORMATION: Synthesized DNA

<400> SEQUENCE: 9
tggatctttg ac                                              12

<210> SEQ ID NO 10
<211> LENGTH: 12
<212> TYPE: DNA
<213> ORGANISM: Artificial Sequence
<220> FEATURE:
<223> OTHER INFORMATION: Synthesized DNA

<400> SEQUENCE: 10
aacatctccg gg                                              12
```